(12) United States Patent
Giovannini et al.

(10) Patent No.: US 11,104,670 B2
(45) Date of Patent: Aug. 31, 2021

(54) 4-PYRIMIDIN-5-YLMETHYL-MORPHOLINE DERIVATIVES AND THE USE THEREOF AS MEDICAMENT

(71) Applicant: Boehringer Ingelheim International GmbH, Ingelheim am Rhein (DE)

(72) Inventors: Riccardo Giovannini, Biberach an der Riss (DE); Angelo Ceci, Mittelbiberach (DE); Cornelia Dorner-Ciossek, Warthausen (DE); Roland Pfau, Biberach an der Riss (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/654,031

(22) Filed: Oct. 16, 2019

(65) Prior Publication Data
US 2020/0123140 A1  Apr. 23, 2020

(30) Foreign Application Priority Data

Oct. 17, 2018 (EP) ..................................... 18200975

(51) Int. Cl.
| | | |
|---|---|---|
| *A61K 31/5355* | (2006.01) | |
| *A61P 25/00* | (2006.01) | |
| *C07D 413/06* | (2006.01) | |
| *A61K 45/06* | (2006.01) | |

(52) U.S. Cl.
CPC ............ *C07D 413/06* (2013.01); *A61K 45/06* (2013.01)

(58) Field of Classification Search
CPC .... C07D 413/06; A61K 31/5355; A61P 25/00
See application file for complete search history.

(56) References Cited

U.S. PATENT DOCUMENTS

2002/0055519 A1   5/2002  Thompson et al.

FOREIGN PATENT DOCUMENTS

| WO | 2003010159 A1 | 2/2003 |
| WO | 2010088408 A2 | 8/2010 |
| WO | 2014060398 A1 | 4/2014 |
| WO | 2015130905 A1 | 9/2015 |
| WO | 2016029146    | 2/2016 |

OTHER PUBLICATIONS

International Search Report and Written Opinion for PCT 2018/083728 dated Feb. 4, 2019.
Murrough, "Antidepressant Efficacy of Ketamine in Treatment-Resistant Major Depression: A Two Site Randomized Controlled Trial", Am. J. Psychiatry, 2013, vol. 170, p. 1134-1142.
Singh, "Intravenous Eskatamine in Adult Treatment-Resistant Depression: A double-Blind, Double-Randomization, Placebo Controlled Study", Society of Biological Psychiatry, vol. 80, 2016, p. 424-431.
Berman, "Antidepressant effects of Ketamine in depressed patients", Biological Psychiatry, vol. 47, 2000, p. 351-354.
Krystal, "Subanesthetic Effects of the Noncompetitive NMDA Antagonist, Ketamine in Humans", Arch. Gen. Psychiatry, 1994, vol. 51, p. 199-214.
Paoletti, NMDA receptor subunit diversity: impact on receptor properties, synaptic plasticity and disease, Nature Reviews, vol. 14, 2013.
Miller, "GluN2B-contaning NMDA receptors regulate depression-like behavior and are critical for the rapid antidepressant actions of ketamine", eLife3e03581, 2014.
Kiselycznyk, "NMDA receptor subunits and associated signaling molecules mediating anti-depressant related effects of NMDA-GluN2B antagonism", Bhav. Nrain Res. 2015, p. 89-95.
Jimemez-Sanchez, "The Role of GluN2A and GluN2B Subunits on the effects of NMDA receptor Antagonists in modeling Schizophrenia and treating Refractory Depression", Neuropsychopharmacology, 2014.
Taylor, "Absolute Oral Bioavailability of Traxoprodil in Cytochrome P450 2D6 Extensive and Poor Metabolisers", Clin. Pharmacokinet, 2006, vol. 45, p. 989-1001.
Addy, "Single dose Administration of MK-0657, an NR2B-Selective NMDA Antagonist", J. of Clinical Pharmacology, 2009, p. 856-864.
Layton, "Discovery of 3-Substituted Aminocyclopentanes as Potent and Orally Bioavailable NR2B Subtype-Selective NMDA Antagonists", ACS Chem. Neuroscience, 2011.
Traynelis, Glutamate Receptor Ion Channels: Structure, Regualtion and Function, Pharmacology reviews, 2010, vol. 62.
Chaffey, NMDA receptor subtypes, Current Anesthesia and Critical Care, 2008, vol. 19, p. 183-201.

(Continued)

*Primary Examiner* — Brenda L Coleman
(74) *Attorney, Agent, or Firm* — David L. Kershner

(57) ABSTRACT

Disclosed are 4-pyrimidin-5-ylmethyl-morpholines of formula A

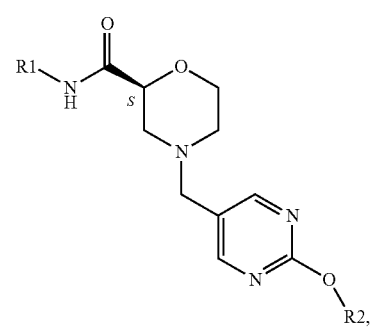

and pharmaceutically acceptable salts thereof, wherein $R^1$ and $R^2$ are defined herein. Also disclosed are processes for their preparation, pharmaceutical compositions containing the compounds, and their use in therapy, particularly in the treatment or prevention of conditions having an association with NR2B negative allosteric modulating properties.

11 Claims, 2 Drawing Sheets

(56) References Cited

OTHER PUBLICATIONS

Mony, Allosteric modulators of NR-2B-containing NMDA receptors, Bristish Journal of Pharmacology, vol. 157, 2009.
Preskorn, An Innovative Design to Establish Proof of Concept of the Antidepressant effects of the NR2B Subunit Selective N-Methyl D-Aspartate Antagonist CP-101, 606, Journal of Clinical Pharmacology, vol. 28, 2008.
Beinat, Insights into Structure related activity relationships, Current Medicinal Chem, 2010. vol. 17, p. 4166-4190.
Serafini, The Role of Ketamine in Treatment resistant Depression, Current Neurapharmacology, 2014, vol. 10, p. 444-461.

P1 – pulse 1; P25 – pulse 25.

4-PYRIMIDIN-5-YLMETHYL-MORPHOLINE DERIVATIVES AND THE USE THEREOF AS MEDICAMENT

FIELD OF THE INVENTION

The present invention relates to novel 4-pyrimidin-5-ylmethyl-morpholine derivatives, processes for their preparation, pharmaceutical compositions containing them and their use in therapy, particularly in the treatment or prevention of conditions having an association with NR2B negative allosteric modulating properties.

The compounds of the invention according to general formula A show NR2B negative allosteric modulating properties.

BACKGROUND OF THE INVENTION

Extensive studies over the past twenty years have indicated that N-methyl-D-aspartate receptors (NMDA) play a relevant role in Alzheimer's disease, Parkinson's disease, dyskinesia, stroke, motor neuron disease, psychosis, epilepsy, anxiety, schizophrenia and pain.

The non-selective NMDA receptor antagonist ketamine, (racemic as well as the S enantariomer), a medication mainly used for starting and maintaining anaesthesia, has demonstrated over the last years clinical efficacy in treating major depressive disorder (MDD) at subanaesthetic doses (Murrough et al. 2013, Am J Psychiatry. 170: 1134; Singh et al. 2016, Biol Psychiatry. 80: 424). More precisely, ketamine elicits a rapid onset of efficacy which lasts several days in MDD patients insufficiently responding to standard drug therapy (Berman et al. 2000. Biol Psychiatry 47:351, Serafini et al. 2014. Curr. Neuropharmacol.12:444). However, non-selective NMDA receptor antagonists have a range of undesirable effects which limit their application. In particular dissociative and psychogenic side effects are prominent for the non-selective NMDA receptor antagonists such as ketamine (Krystal et al. 1994. Arch. Gen. Psychiatry 51:199). In the early 1990s, it was found that multiple NMDA receptor subtypes exist, which contain different NR2(A-D) subunits (Paoletti et al., 2013 Nat Rev. Neurosci 14:383). More recently, NR2B subtype selective NMDA receptor negative allosteric modulators (NR2B NAM) have raised interest and have shown potential in a wide range of clinical indications, such as attention, emotion, mood, and pain, as well as being involved in a number of different human disorders (Mony et. al. 2009. Br. J. Pharmacol. 157:1301; Chaffey et al., Current Anaesthesia & Critical Care 19, 183). In particular, NR2B NAM have also demonstrated antidepressant efficacy in the early stage of clinical trials (Preskorn et al. 2008. J Clin Psychopharmacol 70:58). Preclinical studies using NR2B NAM as well as applying various transgenic mice strains have shown that NR2B containing NMDA-receptors are mediating the positive effect of ketamine in e.g. the Forced Swim Test (Miller et al. 2014 eLife 3:e03581; Kiselycznyk et al. 2015, Behav Brain Res, 287:89). Furthermore, selective NR2B NAM have advantages over unselective NMDA receptor antagonists, such as ketamine, due to greatly diminished dissociative and psychotomimetic side effects (Jimenez-Sanchez et al. 2014. Neuropsychopharmacology 39:2673). NR2B NAM described to date have exhibited drawbacks with regard to their receptor pharmacology and/or to other drug properties which have limited potential use in human drug therapy (Taylor, et al., 2006, Clin Pharmacokinet.45: 989; Addy et al. 2009 J of Clinical Pharmacology 49:856)).

WO2015/130905 discloses compounds of formula (I)

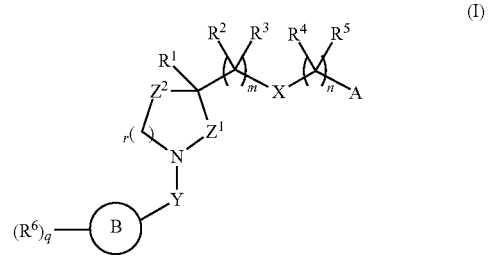

that are inhibitors of Nav1.6 useful in the treatment of multiple sclerosis, polyneuritis, multiple neuritis, amyotrophic lateral sclerosis, Alzheimer's disease or Parkinson's disease. WO2015/130905 discloses the specific examples 100, 105, 106 and 107 in which ring B corresponds to a meta-disubstituted phenyl ring.

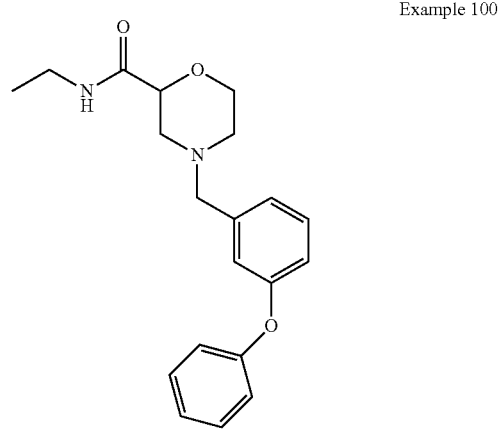

Example 100

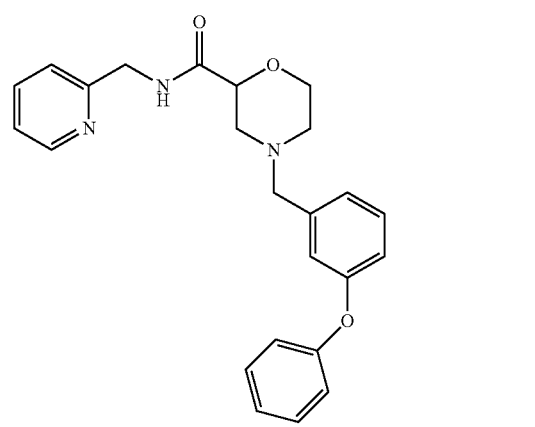

Example 105

Example 106

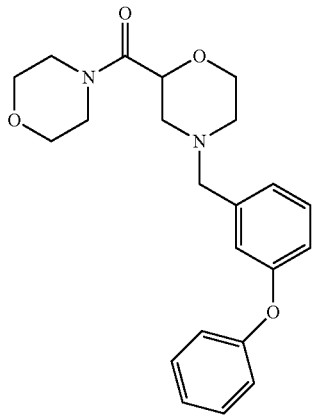

Example 107

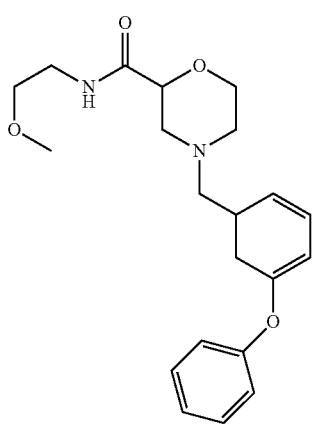

WO2015/130905 reports specific examples 100, 105, 106 and 107 to be weak Nav1.6 inhibitors (Nav 1.6 blockage of examples 100, 105 and 107 at 1-5 µM, and Nav 1.6 blockage of example 106 at >5 µM).

SUMMARY OF THE INVENTION

The present invention relates to novel 4-pyrimidin-5-ylmethyl-morpholines of formula A

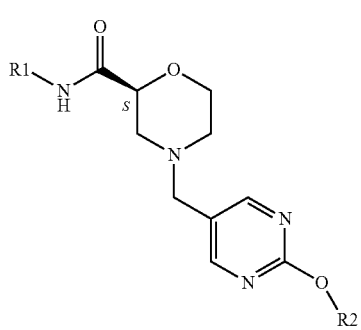

in which
$R^1$ represents methyl, ethyl, propyl, iso-propyl, cyclopropyl, $H_3C—CH_2—CH_2—CH_2—$, cyclobutyl;
$R^2$ represents phenyl which is optionally substituted with 1, 2 or 3 substituents selected from the group consisting of fluoro, chloro, methyl, ethyl, cyclopropyl;

or a salt thereof, particularly a pharmaceutically acceptable salt thereof.

In another embodiment, in the general formula A, $R^2$ has the same meaning as defined in any of the preceding embodiments, and
$R^1$ represents methyl.

In another embodiment, in the general formula A, $R^1$ has the same meaning as defined in any of the preceding embodiments, and
$R^2$ represents

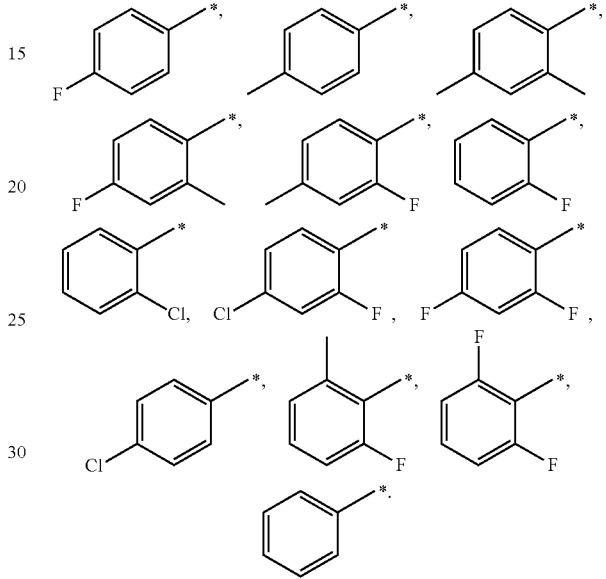

Compounds of the present invention are generically encompassed by formula (I) of WO2015/130905. The compounds of the present invention differ structurally from the examples 100, 105, 106 and 107 explicitly disclosed in WO2015/130905 in that they contain a para-disubstituted pyrimidinyl substructure in place of the meta-disubstituted phenyl ring.

The structural differences unexpectedly result in potent NR2B negative allosteric modulators (see Table 1), whereas the specific examples 100, 105, 106 and 107 of WO2015/130905 do not show any activity on the NR1-NR2B ion channel (see Table 2). Furthermore, compounds of the present invention do not inhibit Nav 1.6 at concentrations at which specific examples 100 and 105 of WO2015/130905 inhibit Nav 1.6 (5 µM; see Tables 3 and 4).

Further, the compounds of the present invention show good membrane permeability and no in vitro efflux (see Table 5 for MDCK assay MDR1 (P-gp)). Therefore, compounds of the present invention are expected to show a favorable brain penetration which is required for efficacious CNS medicaments.

The MDCK assays provide information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1. Identical or similar permeabilities in both transport directions indicate passive permeation (PEBA/PEAB≤1), vectorial permeability points to additional active transport mechanisms. Higher PEBA than PEAB (PEBA/PEAB>5) indicates the involvement of active efflux mediated by MDR1, which might compromise the goal to achieve sufficient brain exposure. Therefore, this assay provides valuable support for selection of compounds applicable for further in vivo testing. High permeability not limited by efflux at the blood brain barrier is a favourable characteristic for compounds that are to be used for drugs acting primarily in the CNS.

Further, the compounds of the present invention are metabolically stable in human liver microsomes (see Table 6, metabolic stability). Therefore, compounds of the present invention are expected to have a favorable in vivo clearance and thus the desired duration of action in humans.

Stability in human liver microsomes refers to the susceptibility of compounds to biotransformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolism in vitro. Enhanced stability in human liver microsomes is associated with several advantages, including increased bioavailability and adequate half-life, which can enable lower and less frequent dosing of patients. Thus, enhanced stability in human liver microsomes is a favorable characteristic for compounds that are to be used for drugs.

Consequently, compounds of the present invention must be more viable for human use.

The objective technical problem is thus to provide potent and selective NR2B negative allosteric modulators.

DETAILED DESCRIPTION OF THE INVENTION

Figure 1:
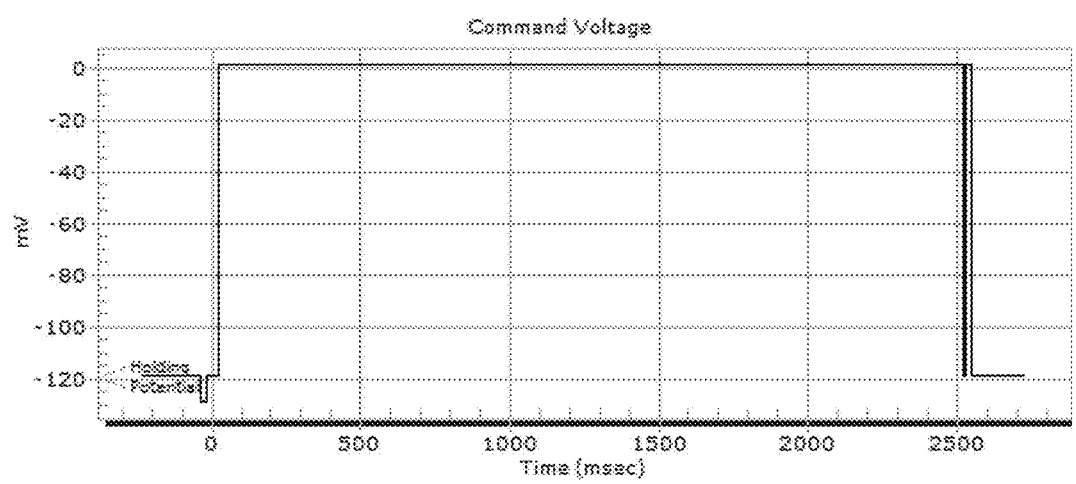
FIG. 1 shows Tetracaine inhibition of Nav1.6.

The present invention provides novel 4-Pyrimidin-5-yl-methyl-morpholines of general formula A that unexpectedly are potent and selective negative allosteric modulators of NR2B.

Another aspect of the invention refers to compounds according to formula A as potent and selective NR2B negative allosteric modulators having high membrane permeability and no in vitro efflux.

Another aspect of the invention refers to compounds according to formula A as potent and selective NR2B negative allosteric modulators having high metabolic stability in human liver microsomes.

Another aspect of the invention refers to compounds according to formula A as potent and selective NR2B negative allosteric modulators having high membrane permeability, no in vitro efflux, and high metabolic stability in human liver microsomes.

Another aspect of the invention refers to pharmaceutical compositions, containing at least one compound according to formula A optionally together with one or more inert carriers and/or diluents.

A further aspect of the present invention refers to compounds according to formula A, for the use in the prevention and/or treatment of disorders associated with NR2B negative allosteric modulators.

Another aspect of the invention refers to processes of manufacture of the compounds of the present invention.

Preparation

The following schemes shall illustrate generally how to manufacture the compounds according to general formula A and the corresponding intermediate compounds by way of example. The abbreviated substituents may be as defined above if not defined otherwise within the context of the schemes.

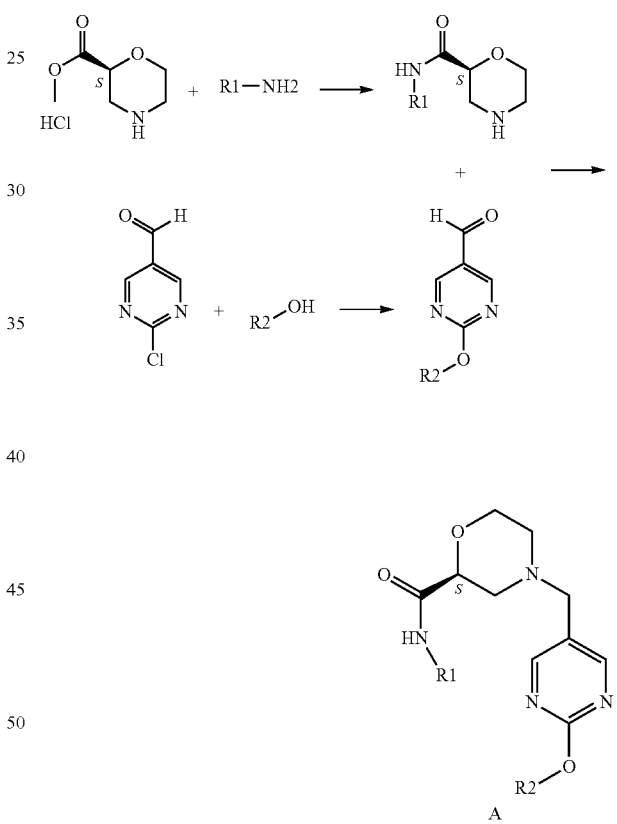

Scheme 1 illustrates the synthesis of pyrimidine derivatives of general formula A. The first step is a nucleophilic substitution of a substituted phenol derivate R2-OH and 2-chloro-pyrimidine-5-carbaldehyde; the last step is represented by a reductive amination involving the aldehyde and a slight excess of an amide derivative of the (S)-Morpholine-2-carboxylic acid obtained by reacting (S)-Morpholine-2-carboxylic acid methyl ester with the corresponding amine.

The described synthetic approach can be used also for gram scale synthesis applying different purification techniques such as crystallization or column chromatography.

General Definitions

Terms not specifically defined herein should be given the meanings that would be given to them by one skilled in the art in light of the disclosure and the context.

NR2B ion channel should be understood as NMDA receptor containing the NR2B protein.

In case a compound of the present invention is depicted in form of a chemical name as well as a formula, the formula shall prevail in case of any discrepancy.

An asterisk may be used in sub-formulas to indicate the bond which is connected to the core molecule or to the substituent to which it is bound as defined.

The term "substituted" as used herein means that any one or more hydrogens on the designated atom is replaced with a selection from the indicated group, provided that the designated atom's viable valence number is not exceeded, and that the substitution results in a stable compound.

Stereochemistry:

Unless specifically indicated, throughout the specification and the appended claims, a given chemical formula or name shall encompass rotamers, tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist.

Salts:

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt or a complex with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

Biological Assays and Data

List of Abbreviations

DMEM Dulbecco's Modified Eagle's Medium
FBS fetal Bovine Serum
FLIPR fluorometric imaging plate reader
HEK293 cell line derived from human embryonic kidney cells
HEPES hydroxyethyl-piperazineethane-sulfonic acid buffer
IC50 half maximal inhibitory concentration
MDCK Madin-Darby canine kidney
MDR1 Multi drug resistance protein 1
P-gp p-Glycoprotein
SEM standard error mean
EGTA ethylene glycol-bis(β-aminoethyl ether)-N,N,N', N'-tetraacetic acid, also known as egtazic acid In-Vitro Effect:

Determination of In Vitro Pharmacological Activity

The activity of the compounds of the invention may be demonstrated using the following in vitro NMDA NR1/NR2B cell assays:

Method:

A human HEK293 cell line with tetracyclin-inducible expression of NMDA NR1/NR2B receptor was used as a test system for compound efficacy and potency. The cell line was purchased from ChanTest, Catalog #CT6121. Compound activity was determined by measuring the effect of compounds on intracellular calcium concentration induced by glycine/glutamate agonism in a FLIPRtetra system (Molecular Devices).

Cell Culture:

The cells were obtained as frozen cells in cryo-vials and stored until use at −150° C. Cells were grown in culture medium (DMEM/F12, 10% FBS, 5 µg/mL Blasticidin, 150 µg/mL Zeozin, 500 µg/mL Geneticin). It is important that density does not exceed 80% confluence. For sub-culturing the cells were detached from flasks by Versene. For the assay, cells were detached, washed twice with induction medium (DMEM/F12 without glutamine, 10% FBS, 2 µg/mL Tetracycline, 2 mM Ketamine) and seeded to 384 well pure coat amine plates (Becton Dickinson, 50000 cells per well in 50 µl) 48 h prior to assay in induction medium.

Compound Preparation

The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions were prepared in duplicate, further intermediate dilutions (1:37.5) of the substances were carried out with aqueous assay buffer (137 mM NaCl, 4 mM KCl, 1.8 mM $CaCl_2$), 10 mM HEPES, 10 mM Glucose, pH 7.4) resulting in a compound concentration 3 times above the final test concentration and DMSO at 2.7% resulting in 0.9% final DMSO concentration in the assay.

FLIPR Assay:

At the assay day cells were washed 3× with assay buffer (as described above), 10 µL buffer remained in the wells after washing. 10 µL Ca kit loading buffer (AAT Bioquest; prepared from the kit containing the following components: Component A: Fluo-8 NW dissolved in 200 µL DMSO and 20 µl of this solution are mixed with 10 ml buffer prepared out of component B and C, Component B: 10× Pluronic® F127 Plus diluted 1:10 in component C, Component C: HHBS (Hanks with 20 mM Hepes) was added to the cells and the plates were incubated with lid for 60 minutes at room temperature. 20 µl assay buffer containing 60 µM glycine (20 µM final) and 3 µM glutamate (1 µM final) was added to column 1-23, column 24 got assay buffer without glycine/glutamate to serve as negative unstimulated control. Fluorescence (indicating the calcium influx as a result of the NR1/NR2B ion channel activation) was read on the FLIP-Rtetra device for 60 seconds to monitor the glutamate induced effects. After 2 minutes 20 µL of compound dilution prepared as described above or controls (row 1-22) in assay buffer were carefully added to the wells. Fluorescence was read on the FLIPR tetra device for additional 6 minutes to monitor the compound induced effects after activation by agonists. The average of 2 measurements at 5 minutes and 5 min 10 seconds after compound addition is calculated and further used for IC50 calculations. Each assay microtiter compound dilution plate contained wells (in column 23 or 24) with DMSO controls instead of compound as controls for glycine/glutamate induced fluorescence (high controls) and wells with 1 µM of a reference NR2B NAM as low controls (Compound 22; reference: Layton, Mark E et al, ACS Chemical Neuroscience 2011, 2(7), 352-362).

Data Evaluation and Calculation:

The output file of the reader contains the well number and measured average fluorescence units. For data evaluation and calculation, the measurement of the low control was set as 0% control and the measurement of the high control was set as 100% control. The IC50 values were calculated using the standard 4 parameter logistic regression formula. Calculation: [y=(a−d)/(1+(x/c)^b)+d], a=low value, d=high value; x=conc M; c=IC50 M; b=slope.

NR2B negative allosteric modulators covered by general structure A and exhibiting a low $IC_{50}$ value are preferred.

TABLE 1

In vitro NR2B affinity of the compounds of the present invention as obtained in the FLIPR assay.

| Example number | IC50 [nM] |
| --- | --- |
| 20 | 133 |
| 21 | 702 |
| 22 | 1107 |
| 23 | 143 |
| 24 | 98 |
| 25 | 216 |
| 26 | 550 |
| 27 | 350 |
| 28 | 500 |
| 32 | 547 |
| 33 | 509 |
| 34 | 362 |
| 35 | 933 |

TABLE 2

In vitro NR2B affinity of the closest prior art compounds (examples 100, 105, 106 and 107 in WO2015/130905) as obtained in the same FLIPR assay as compounds in Table 1.

| Example number in WO2015/130905 | IC50 [nM] |
| --- | --- |
| 100 | >8887 |
| 105 | >9261 |
| 106 | >9255 |
| 107 | >9257 |

Determination of Nay 1.6.Inhibition

Equipment:

Ion Works Quattro electrophysiological platform

Compound Plate Preparation

The compounds were prepared in DMSO at 300× the final assay concentrations of 1 and 5 µM.

The 300× DMSO stock solutions were transferred into assay plates where 2 µl per well of each 300× stock solution were placed. All assay plates were stored at −80° C. until the day of assay.

On the day of the assay, the appropriate assay plate was thawed at room temperature, centrifuged, and 198 µl of external recording solution was added and mixed thoroughly. This provided a 1:100 dilution. A further 1:3 dilution occurred upon addition to the cells in the IonWorks Quattro electrophysiological platform, giving a 1:300 dilution in total.

On each assay plate, at least 8 wells were reserved for vehicle control (0.3% DMSO) and at least 8 wells for each positive control specific to the cell line tested. The positive controls were tested at a maximal blocking and an approximate IC50 concentration. As positive control Lidocaine at concentrations of 30 and 1000 µM was used.

Electrophysiological Recording Solutions

The solutions for recording Nav1.6 currents were as follows:

External Recording Solution

NaCl 137 mM

KCl 4 mM $MgCl_2$ 1 mM $CaCl_2$ 1.8 mM

HEPES 10 mM

Glucose 10 mM pH 7.3 (titrated with 10M NaOH)

Internal Recording Solution

CsF 90 mM

CsCl 45 mM

HEPES 10 mM

EGTA 10 mM pH 7.3 (titrated with 1M CsOH)

Amphotericin B was used to obtain electrical access to the cell interior at a final concentration of 200 µg/ml in internal recording solution.

Experimental Protocols & Data Analysis

Nav1.6 Experimental Protocol

State-dependent inhibition: Sodium channels when held at depolarized potential or long test pulse, the channels open and inactivate and then stay inactivated until the membrane potential is stepped back to hyperpolarized potentials, when the inactivated channels recover from inactivation into closed state. An example is Tetracaine inhibition (FIG. 1), which is much stronger at depolarized potentials than at hyperpolarized potential.

Nav1.6 Data Analysis

Cells were held at −120 mV. In order to completely inactivate the sodium channels (pulse 1), the cells were pulsed to +0 mV for 2500 ms and stepped back to −120 mV for 10 ms (to completely recover from inactivation, however channels that had drugs bound to them will not recover from inactivation) before stepping to +0 mV for 20 ms (pulse 2).

IonChannel Profiler Data Filters

| Data Filter | Platform | Criteria |
|---|---|---|
| Seal Quality | IonWorks Quattro | >30 MΩ |
| Seal Drop | IonWorks Quattro | <50% Seal Drop (Seal Pre-Compound/Seal Post Compound) |
| Current Amplitude | IonWorks Quattro | >200 pA |

Assay Control Results

Both the positive and vehicle control data associated with each cell line assayed are shown below as an example. The mean is shown for each positive and negative control as solid symbol with the total number of individual well replicates given next to the solid symbol. In addition, the individual data of each well are shown on the graph as open symbols so that the variation about the mean value can be readily assessed. These data are provided to aid in determining whether a compound has activities on the ion channel relative to the control data and provides an indication of assay variability and accordingly is used to judge the effect size of a compound-specific effect that can be detected.

Shown below are the assay controls for the Nav1.6 IonWorks Quattro assay. Lidocaine, a Nav1.6 reference compound, inhibited evoked currents in a concentration and use dependent manner as predicted (FIG. 2).

Figure 2:
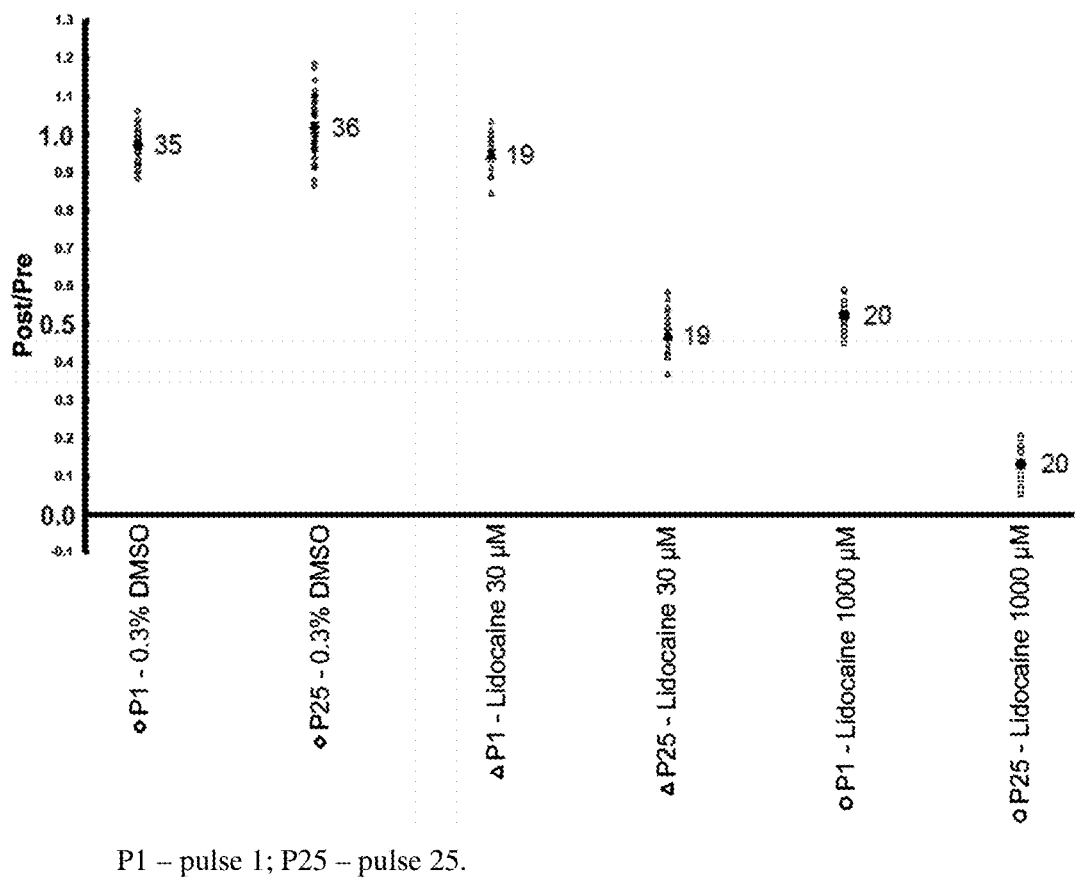
FIG. 2 shows the inhibition of evoked currents in a concentration and use dependent manner using Lidocaine as reference compound.

In FIG. 2, a Post/Pre value of 1.0 corresponds to 0% inhibition, a Post/Pre value of 0.0 corresponds to 100% inhibition. To illustrate the variation of the assay, both example 106 of WO2015/130905 showing 14% inhibition of Nav 1.6 at 5 μM (normalized, see Table 3) and example 25 of the present invention showing −18.8% inhibition of Nav 1.6 at 5 μM (normalized, see Table 4), respectively, are within the variation of the assay when compared to assay control data, and are therefore not showing any significant inhibition of the Nav 1.6 channel at 5 μM.

Tables 3 and 4 show the normalized percentage inhibition of Nav1.6 channel. The normalized data show the compound data normalized to vehicle control (0% inhibition) and maximal inhibition control (100% inhibition); maximum inhibition at P1 by 1000 μM lidocaine (not normalized) was ranging from 46.4% to 47.2% across the experiments. (see also the figure Assay Control Results above).

TABLE 3

Normalized in vitro Nav 1.6 inhibition of the closest prior art compounds (examples 100, 105, 106 and 107 in WO2015/130905) as obtained in the same electrophysiology assay as compounds in Table 4 (concentrations: 1 μM and 5 μM).

| Example number in WO2015/130905 | Normalized % inhibition at 1 μM | Normalized % inhibition at 5 μM | Percentage SEM at 1 μM | Percentage SEM at 5 μM |
|---|---|---|---|---|
| 100 | 2.2 | 37.8 | 6.2 | 8.4 |
| 105 | 18.2 | 68 | 2.6 | 4.1 |
| 106 | −0.7 | 14 | 1.6 | 0.4 |
| 107 | −8.5 | 13.1 | 3.9 | 2.8 |

TABLE 4

Normalized in vitro Nav 1.6 inhibition of the compounds of the present invention as obtained in the same electrophysiology assay as prior art compounds in Table 3 (concentrations: 1 μM and 5 μM).

| Example number | Normalized % inhibition at 1 μM | Normalized % inhibition at 5 μM | Percentage SEM at 1 μM | Percentage SEM at 5 μM |
|---|---|---|---|---|
| 20 | −8.9 | −10.1 | 3.1 | 3.5 |
| 21 | 1.3 | 3.6 | 2.4 | 3.2 |
| 22 | 3.8 | −10.4 | 2.5 | 2.8 |
| 23 | 0.1 | 2.9 | 5.7 | 3.8 |
| 24 | 5.8 | −3.7 | 3.3 | 2.6 |
| 25 | −11.8 | −18.8 | 5.4 | 1.3 |
| 26 | 12.8 | 5.7 | 0.3 | 4.0 |
| 27 | −3.1 | 4.3 | 8.7 | 7.0 |
| 28 | −6.2 | −14.6 | 6.0 | 4.0 |
| 32 | −7.7 | −13.5 | 2.1 | 3.7 |

NR2B negative allosteric modulators covered by general structure A which are not showing any significant Nav1.6 inhibition are preferred.

The compounds of the present invention do not show any significant inhibition of the Nav 1.6 channel at 1 and 5 μM, respectively (see Table 4 and Assay Control Results), whereas examples 100 and 105 of WO2015/130905 show 37.8% and 68% inhibition of Nav 1.6 at 5 μM, respectively (see Table 3). Examples 106 and 107 of WO2015/130905 do not show any significant inhibition of the Nav 1.6 channel at 1 and 5 μM, respectively (i.e. inhibition is within assay variability, see Table 3 and Assay Control Results).

MDCK Assay P-Gp

Apparent permeability coefficients (Papp) of the compounds across the MDCK-MDR1 monolayers (MDCKII cells transfected with human MDR1 cDNA expression plasmid) are measured in apical-to-basal (AB) and basal-to-apical (BA) direction.

MDCK-MDR1 cells ($6 \times 10^5$ cells/cm$^2$) are seeded on filter inserts (Corning, Transwell, polycarbonate, 0.4 μm pore size) and cultured for 9 to 10 days. Compounds dissolved in DMSO stock solution (1-20 mM) are diluted with HTP-4 aqueous buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$, 0.41 mM NaH$_2$PO$_4$, 15 mM HEPES, 20 mM glucose, pH 7.4) supplemented with 0.25% BSA to prepare the transport solutions (final concentration: 1 or 10 μM, final DMSO <=0.5%). The transport solution is applied to the apical or basolateral donor side for measuring A-B or B-A permeability, respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS (RapidFire High-throughput MS System (Agilent) coupled to QTrap 6500 (AB Sciex) or TSQ Vantage (Thermo Scientific)). Sampled receiver volumes are replaced with fresh receiver solution. Efflux ratio is calculated dividing the Papp (b-a) values by the Papp (a-b) values. Results are shown in Table 5.

TABLE 5

| Ex. | Papp (a-b) mean [10−6 cm/s] | efflux ratio PEBA/PEAB |
|---|---|---|
| 20 | 80 | 0.7 |
| 21 | 56 | 1.0 |
| 22 | 57 | 0.7 |

TABLE 5-continued

| Ex. | Papp (a-b) mean [10−6 cm/s] | efflux ratio PEBA/PEAB |
|---|---|---|
| 23 | 65 | 0.9 |
| 24 | 56 | 0.8 |
| 25 | 88 | 0.5 |
| 26 | 95 | 0.6 |
| 27 | 54 | 0.7 |
| 28 | 83 | 0.5 |
| 32 | 82 | 0.5 |

The experimental results above show that compounds of the present invention are potent NR2B NAMs having high membrane permeability and no in vitro efflux anticipating excellent capability to cross the blood brain barrier.

Metabolic Stability

The metabolic degradation of the test compound was assayed at 37° C. with pooled human liver microsomes. The final incubation volume of 60 µl per time point contains TRIS buffer pH 7.6 at room temperature (0.1 M), magnesium chloride (5 mM aqueous solution), microsomal protein (1 mg/mL for human) and the test compound at a final concentration of 1 µM. Following a short preincubation period at 37° C., the reactions were initiated by addition of betanicotinamide adenine dinucleotide phosphate, reduced form (NADPH, 1 mM), and terminated by transferring an aliquot into acetonitril after different time points. After centrifugation (10000 g, 5 min), an aliquot of the supernatant was assayed by HPLC-MS/MS as described above for the MDCK assay P-gp for the amount of parent compound. The half-life was determined by the slope of the semi-logarithmic plot of the concentration-time profile. Results are shown in Table 6.

TABLE 6

| Ex. | Half-life - t½ [min] human liver microsomes |
|---|---|
| 20 | >130 |
| 21 | >130 |
| 22 | >130 |
| 23 | >130 |
| 24 | >130 |
| 25 | >130 |
| 26 | >130 |
| 27 | >130 |
| 28 | >130 |
| 32 | >130 |

The experimental results above show that compounds of the present invention are potent NR2B NAMs having high stability in human liver microsomes.

The present invention provides compounds according to formula A that unexpectedly result in a favorable combination of the following key parameters:
1) potent and selective negative allosteric modulation of NR2B,
2) high stability in human liver microsomes, and
3) high permeability and no in vitro efflux at MDCK-MDR1 cell transporters.

Pharmaceutical Composition

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Use in Treatment/Method of Use

Human therapeutic applications of NR2B NAM have been summarized in reviews by Traynelis et al. (Traynelis et al., Pharmacology Reviews, 2010, 62:405), Beinat et al. (Beinat et al., Current Medicinal Chemistry, 2010, 17:4166) and Mony et al. (Mony et al., British J. Pharmacology, 2009, 157:1301).

The present invention relates to compounds which are useful in the treatment of psychiatric disorders, diseases and conditions wherein negative allosteric modulation of NR2B is of therapeutic benefit, including: (1) mood disorders and mood affective disorders; (2) schizophrenia spectrum disorders; (3) neurotic, stress-related and somatoform disorders including anxiety disorders; (4) disorders of psychological development; (5) behavioral syndromes associated with physiological disturbances and physical factors; (6) substance-related and addictive disorders; (7) disease associated with symptoms of negative and positive valence; (8) pain; (9) cerebrovascular diseases; (10) episodic and paroxysmal disorders; (11) neurodegenerative diseases.

In view of their pharmacological effect, compounds of the present invention are suitable for use in the treatment of a disorder, disease or condition selected from the list consisting of (1) treatment of mood disorders and mood affective disorders including bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, catatonia.

(2) treatment of mood disorders belonging to the schizophrenia spectrum and other psychotic disorders including schizophrenia and schizoaffective disorder with associated negative and cognitive symptoms.

(3) treatment of disorders belonging to the neurotic, stress-related and somatoform disorders including anxiety disorders, general anxiety disorder, panic disorder with or without agoraphobia, specific phobia, social phobia, chronic anxiety disorders; obsessive compulsive disorder; reaction to sever stress and adjustment disorders, such as post-traumatic stress disorder; other neurotic disorders such as depersonalisation-derealisation syndrome.

(4) treatment of disorders of psychological development including pervasive developmental disorders, including Asperger's syndrome and Rett's syndrome, autistic disorders, childhood autism and overactive disorder associated with mental retardation and stereotyped movements, specific developmental disorder of motor function, specific developmental disorders of scholastic skills, attention deficit/hyperactivity disorder.

(5) treatment of behavioral syndromes associated with physiological disturbances and physical factors including mental and behavioural disorders associated with the puerperium, including postnatal and postpartum depression; eating disorders, including anorexia nervosa and bulimia nervosa and other impulse control disorders.

(6) treatment of disorders of substance-related and addictive disorders, which are substance use disorders induced by alcohol, cannabis, hallucinogen, stimulant, hypnotic, tobacco.

(7) treatment of disease associated with symptoms of negative and positive valence including anhedonia, sustained threat and loss, suicidal ideation.

(8) treatment of acute and chronic pain which is related to neuropathy, e.g. diabetic neuropathy or polyneuropathy, physiological processes and physical disorders including e.g. low back pain, pain in the joints, disease of the musculoskeletal system and connective tissue, e.g. rheumatism, myalgia, nerve, nerve root and plexus disorders, e.g. phantom limb syndrome with pain, carpal tunnel syndrome.

(9) treatment of cerebrovascular diseases, e.g. intracerebral or subararchnoid haemorrhage, cerebral infarction, stroke, occlusion and stenosis, cerebral atherosclerosis, cerebral amyloid angiopathy.

(10) treatment of episodic and paroxymal disorders, e.g. epilepsy.

(11) treatment of diseases which include forms of neurodegeneration, e.g. stroke, Alzheimer's disease and Huntington's disease.

As used herein, unless otherwise noted, the terms "treating", "treatment" shall include the management and care of a human subject or human patient for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

According to another aspect, the present invention provides a compound of formula A or a pharmaceutically acceptable salt thereof for use in the treatment and/or prevention of the above mentioned conditions.

According to another aspect, the present invention provides a compound of formula A according to any one of the preceding aspects characterized in that the compound of formula A is used in addition to behavioural therapy, TMS (transcranial magnetic stimulation), ECT (electroconvulsive therapy) and other therapies.

Combination Therapy

Compounds according to the present invention can be combined with other treatment options known to be used in the art in connection with a treatment of any of the indications the treatment of which is in the focus of the present invention.

According to another aspect, the present invention provides a compound of formula A according to any one of the preceding aspects characterized in that the compound of formula A is administered in addition to treatment with one or more antidepressant selected from the list consisting of duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, nortriptyline. The term "antidepressant" shall mean any pharmaceutical agent or drug which can be used to treat depression or diseases associated with depressive symptoms.

According to another aspect, the present invention provides a compound of formula A according to any one of the preceding aspects characterized in that the compound of formula A is administered in addition to treatment with one or more antipsychotic selected from the list consisting of aripiprazole, paliperidone palmitate, lurasidone, quetiapine, risperidone, olanzapine, paliperidone, brexpiprazole, clozapine, asenapine, chlorpromazine, haloperidol, cariprazine, ziprasidone, amisulpride, iloperidone, fluphenazine, blonanserin, aripiprazole lauroxil. The term "antipsychotic" shall mean any pharmaceutical agent or drug which can be used to treat diseases associated with psychotic or depressive symptoms.

According to another aspect, the present invention provides a compound of formula A according to any one of the preceding aspects characterized in that the compound of formula A is administered in addition to treatment with one or more psychostimulant selected from the list consisting of lisdexamfetamine, methylphenidate, amfetamine, dexamfetamine, dexmethylphenidate, armodafinil, modafinil. The term "psychostimulant" shall mean any pharmaceutical agent or drug which can be used to treat diseases like mood disorders, or impulse control disorders.

According to another aspect, the present invention provides a compound of formula A according to any one of the preceding aspects characterized in that the compound of formula A is administered in addition to treatment with nootropics selected from the list consisting of oxiracetam, piracetam, or the natural product St John's-wort.

According to another aspect, the present invention provides a compound of formula A which is administered in addition to treatment with one or more antidepressant, antipsychotic, psychostimulant, nootropics or natural product according to any one of the preceding aspects characterized in that the combination of compound of formula A and one or more antidepressant, antipsychotic, psychostimulant, nootropics or natural product is used in addition to behavioural therapy, TMS (transcranial magnetic stimulation), ECT (electroconvulsive therapy) and other therapies.

EXPERIMENTAL SECTION

Abbreviations

ACN acetonitrile
APCI Atmospheric pressure chemical ionization
Boc tert-butyloxycarbonyl
CDI 1,1'-carbonyldiimidazole
CO2 Carbon Dioxide
D day
DA Diode Array
DCM dichloromethane
DIPE diisopropylether
DIPEA diisopropylethylamine
DMF dimethylformamide
e.e. enantiomeric excess
ESI electrospray ionization (in MS)
EtOAc ethylacetate
EtOH ethanol
Ex. example
h hour(s)
HATU O-(7-azabenzotriazol-1-yl)-N,N,N',N'-tetramethyluronium-hexafluorophosphate
HPLC high performance liquid chromatography HPLC-MS coupled high performance liquid chromatography-mass spectrometry M molar (mol/L)

MeOH methanol min minute(s)

MS mass spectrometry

MW molecular weight

NH3 ammonia

PSI Pound per square inch rt room temperature $R_t$ retention time scCO2 supercritical CO2 solv solvent

TBTU O-(Benzotriazol-1-yl)-N,N,N',N'-tetramethyluronium tetrafluoroborate

TEA triethylamine

TFA trifluoroacetic acid

THF tetrahydrofuran

TLC thin-layer chromatography

SFC Supercritical fluid chromatography

Abbreviations within Spectral Data

1H-NMR Proton nuclear magnetic resonance br broad

δ chemical shift d doublet dd doublet of doublets dt doublet of triplets

DMSO-$d_6$ hexa-deutero-dimethylsulfoxide

H proton

Hz Hertz (=1/second)

J coupling constant m multiplet ppm parts per million q quartet s singlet t triplet td triplet of doublets General Analytics.

All reactions were carried out using commercial grade reagents and solvents. NMR spectra were recorded on a Bruker AVANCE IIIHD 400 MHz instrument using TopSpin 3.2 p16 software. Chemical shifts are given in parts per million (ppm) downfield from internal reference trimethylsilane in δ units. Selected data are reported in the following manner: chemical shift, multiplicity, coupling constants (J), integration. Analytical thin-layer chromatography (TLC) was carried out using Merck silica gel 60 F254 plates. All compounds were visualized as single spots using short wave UV light. Low resolution mass spectra were obtained using a liquid chromatography mass spectrometer (LCMS) that consisted of an Agilent 1100 series LC coupled to a Agilent 6130 quadrupole mass spectrometer (electrospray positive ionization).

Methods:

HPLC-MS Methods:

Method 1

Method Name: Z003_S05
Device description: Agilent 1200 with DA- and MS-Detector
Column: XBridge C18_3.0 × 30 mm_2.5 µm
Column producer: Waters
Description:

| Gradient/ Solvent Time [min] | % Sol [Water 0.1% NH₃] | % Sol [Acetonitrile] | Flow [ml/min] | Temp [° C.] | Back pressure [PSI] |
|---|---|---|---|---|---|
| 0.0 | 95.0 | 5.0 | 2.2 | 60.0 | |
| 0.2 | 95.0 | 5.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method 2

Method Name: Z011_S03
Device description: Agilent 1200 with DA- and MS-Detector
Column: XBridge C18_3.0 × 30 mm_2.5 µm
Column producer: Waters
Description:

| Gradient/ Solvent Time [min] | % Sol [Water 0.1% NH₃] | % Sol [Acetonitrile] | Flow [ml/min] | Temp [° C.] | Back pressure [PSI] |
|---|---|---|---|---|---|
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method 3

Method Name: Z017_S04
Device description: Agilent 1200 with DA- and MS-Detector
Column: Sunfire C18_3.0 × 30 mm_1.8 µm
Column producer: Waters
Description:

| Gradient/ Solvent Time [min] | % Sol [Water 0.1% TFA] | % Sol [Acetonitrile] | Flow [ml/min] | Temp [° C.] | Back pressure [PSI] |
|---|---|---|---|---|---|
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Chiral SFC Analytical Methods:

| Method 4: I_SA_20_IPA_NH$_3$_001 | |
|---|---|
| Method Name: | I_SA_20_PA_NH$_3$_001 |
| Device description: | Agilent 1260 SFC with DAD and MS |
| Column: | CHIRAL ART ® Amylose SA_4.6 × 250 mm_5 µm |
| Column producer: | YMC |

| Gradient/ Solvent Time [min] | % Sol [scCO2] | % Sol [ETOH 20 mM NH$_3$] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| Method 5: I_IC_30_IPA_NH$_3$_001 | |
|---|---|
| Method Name: | I_IC_30_IPA_NH$_3$_001 |
| Device description: | Agilent 1260 SFC with DAD and MS |
| Column: | Chiralpak ® IC_4.6 × 250 mm_5 µm |
| Column producer: | Daicel |

| Gradient/ Solvent Time [min] | % Sol [scCO2] | % Sol [MEOH 20 mM NH$_3$] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 7.0 | 30.0 | 4.0 | 40.0 | 2175.0 |

Preparative HPLC Conditions for Purification:
Instrument: (Agilent 1100). Eluents: Water—NH$_4$OH 5% solution in Water—CH$_3$CN; Flow: 50 ml/min; Temperature 60° C.; Column: XBridge C18.

Preparation of Intermediates:

Example 1a

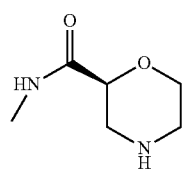

(S)-Morpholine-2-carboxylic acid methyl ester hydrochloride (35 g; 192.7 mmol) was mixed together with 400 ml of a 8M solution of Methylamine in EtOH. The reaction mixture was stirred at room temperature over 60 hours. The solvent was removed under reduced pressure, THF (500 ml) and TEA (50 ml) were added and the reaction mixture stirred at room temperature during 12 hours. A precipitate was formed; the suspension was filtered via a glass filter and the filtrate solution was evaporated under reduced pressure. Obtained 23.5 g of the desired product as solid.

| Example 1: | |
|---|---|
| Chiral SFC Method: I_IC_30_IPA_NH$_3$_001.M | Rt [min]: 3.72; e.e. 100% |
| MS: 145 (M + H)$^+$ | |

Example 6a

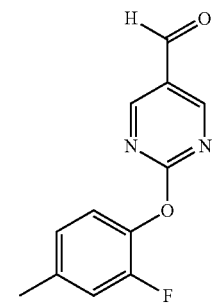 [SMILES: Cc1ccc(Oc2ncc(C=O)cn2)c(F)c1]

2-chloro-pyrimidine-5-carbaldehyde (600 mg; 4.2 mmol) and 2-Fluoro-4-Methyl-phenol (0.5 ml; 4.63 mmol) are dissolved in DMF (5 ml) and K$_2$CO$_3$ (873 mg; 6.3 mmol) is added. The reaction mixture is heated at 80° C. over 2 hours. Water is then added followed by EtOAc (100 ml); the phases are separated and the organic phase is washed two times with a 1N aqueous solution of NaOH (2×50 ml). The organic phase is dried over Na$_2$ SO$_4$ and the crude obtained after evaporation of the solvents is used as such in the next step. Obtained: 740 mg.

| Example 6a |
|---|
| HPLC-MS (Method): Z017_S04 R$_t$ [min]: 0.94    MS: 233(M + H)$^+$ |

Example 6b

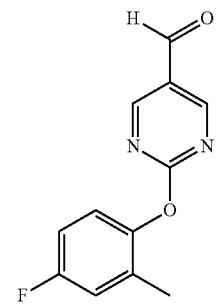 [SMILES: Cc1cc(F)ccc1Oc1ncc(C=O)cn1]

Example 6b is synthesised in analogy to example 6a. Starting materials: 2-chloro-pyrimidine-5-carbaldehyde (600 mg; 4.2 mmol) and 4-Fluoro-2-Methyl-phenol (584 mg; 4.63 mmol). Obtained: 400 mg.

| Example 6b |  |
|---|---|
| HPLC-MS (Method): Z017_S04 $R_t$ [min]: 0.91 | MS: 233 (M + H)+ |

Example 6c

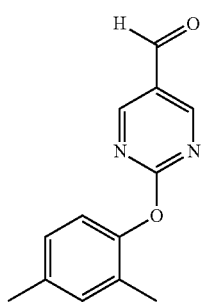 [SMILES: Cc1ccc(Oc2ncc(C=O)cn2)c(C)c1]

Example 6c is synthesised in analogy to example 6a. Starting materials: 2-chloro-pyrimidine-5-carbaldehyde (600 mg; 4.2 mmol) and 2,4-dimethyl-phenol (0.53 ml; 4.42 mmol). Obtained: 800 mg used as such in the next step.

| Example 6c |  |
|---|---|
| HPLC-MS (Method): Z017_S04 $R_t$ [min]: 0.96 | MS: 261 (M + H + MeOH)+ |

Example 6d

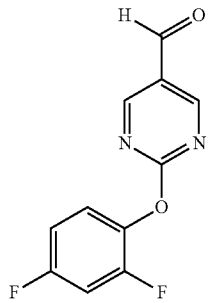 [SMILES: O=Cc1cnc(Oc2ccc(F)cc2F)nc1]

Example 6d is synthesised in analogy to example 6a. Starting materials: 2-chloro-pyrimidine-5-carbaldehyde (600 mg; 4.21 mmol) and 2,4-difluoro-phenol (0.40 ml; 4.2 mmol). Obtained: 340 mg used as such in the next step.

| Example 6d |  |
|---|---|
| HPLC-MS (Method): Z017_S04 $R_t$ [min]: 0.88 | MS: 236 (M)+; 269 (M + H + MeOH)+ |

Example 6e

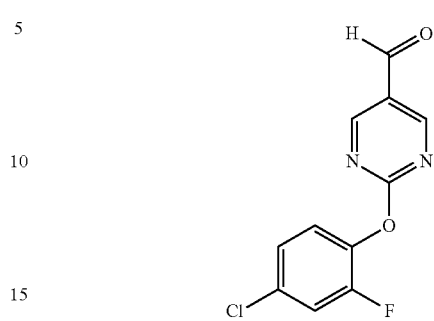

Example 6e is synthesised in analogy to example 6a. Starting materials: 2-chloro-pyrimidine-5-carbaldehyde (600 mg; 4.2 mmol) and 4-chloro-2-Fluoro-phenol (0.49 ml; 4.63 mmol). Obtained: 380 mg used as such in the next step.

| Example 6e |  |
|---|---|
| HPLC-MS (Method): Z017_S04 $R_t$ [min]: 1.02 | MS: 253 and 255 (M + H)+; isotopic pattern for 1 Cl observed |

Example 6f

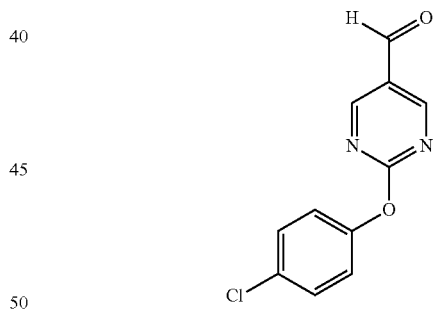

Example 6f is synthesised in analogy to example 6a. Starting materials: 2-chloro-pyrimidine-5-carbaldehyde (600 mg; 4.2 mmol) and 4-chloro-phenol (600 mg; 4.63 mmol). Obtained: 310 mg used as such in the next step.

| Example 6f |  |
|---|---|
| HPLC-MS (Method): Z017_S04 $R_t$ [min]: 0.92 | MS: 267 and 269 (M + H + MeOH)+; isotopic pattern for 1 Cl observed |

Example 6g

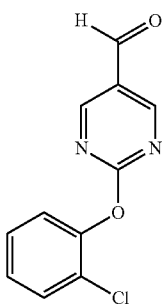 [SMILES: O=Cc1cnc(Oc2ccccc2Cl)nc1]

Example 6g is synthesised in analogy to example 6a. Starting materials: 2-chloro-pyrimidine-5-carbaldehyde (600 mg; 4.2 mmol) and 2-chloro-phenol (0.48 ml; 4.63 mmol). Obtained: 500 mg used as such in the next step.

| Example 6g | |
|---|---|
| HPLC-MS (Method): Z017_S04 $R_t$ [min]: 1.01 | MS: 235 and 237 (M + H)$^+$; isotopic pattern for 1 Cl observed |

Example 6h

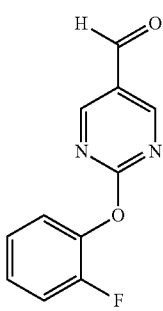

Example 6h is synthesised in analogy to example 6a. Starting materials: 2-chloro-pyrimidine-5-carbaldehyde (600 mg; 4.2 mmol) and 2-fluoro-phenol (0.41 ml; 4.63 mmol). Obtained: 500 mg used as such in the next step.

| Example 6h | |
|---|---|
| HPLC-MS (Method): Z017_S04 $R_t$ [min]: 0.85 | MS: 218 (M)$^+$ |

Example 6i

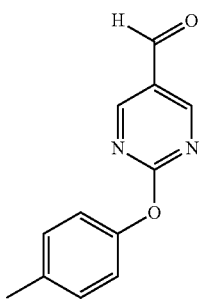 [SMILES: Cc1ccc(Oc2ncc(C=O)cn2)cc1]

Example 6i is synthesised in analogy to example 6a. Starting materials: 2-chloro-pyrimidine-5-carbaldehyde (198 mg; 1.39 mmol) and 4-methyl-phenol (150 mg; 1.39 mmol). Obtained: 278 mg (content 50%) used as such in the next step.

| Example 6i | |
|---|---|
| HPLC-MS (Method): Z017_S04 $R_t$ [min]: 0.855 | MS: 247 (M + H + MeOH)$^+$ |

Example 6j

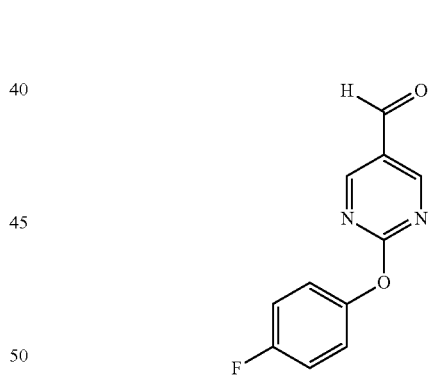

Example 6j is synthesised in analogy to example 6a. Starting materials: 2-chloro-pyrimidine-5-carbaldehyde (600 mg; 4.2 mmol) and 4-fluoro-phenol (0.57 g; 5 mmol). Obtained: 570 mg used as such in the next step.

| Example 6j | |
|---|---|
| HPLC-MS (Method): Z017_S04 $R_t$ [min]: 0.84 | MS: 251 (M + H + MeOH)$^+$ |

Example 6k

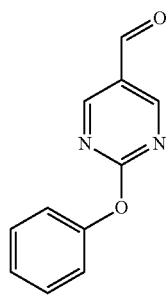 [SMILES: O=Cc1cnc(Oc2ccccc2)nc1]

Example 6k is synthesised in analogy to example 6a. Starting materials: 2-chloro-pyrimidine-5-carbaldehyde (600 mg; 4.21 mmol) and Phenol (0.48 g; 5.05 mmol). Obtained: 380 mg used as such in the next step.

| Example 6k |
| --- |
| HPLC-MS (Method): Z017_S04 R$_t$ [min]: 0.82   MS: 200 (M*)$^+$ |

Example 6l

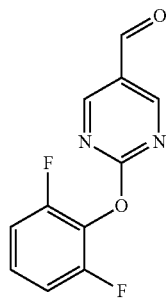 [SMILES: O=Cc1cnc(Oc2c(F)cccc2F)nc1]

2-chloro-pyrimidine-5-carbaldehyde (600 mg; 4.21 mmol) and 2,6-difluorophenol (657 mg; 5.05 mmol) were dissolved in DMF (5 ml) and K$_2$CO$_3$ (873 mg; 6.31 mmol) was added. The reaction mixture was heated at 80° C. for 2 hours. The mixture was diluted with water and extracted with diethylether (70 ml). The organic phase is dried over Na$_2$SO$_4$, filtered and the crude obtained after evaporation of the solvents is used as such in the next step. Obtained: 890 mg of the desired product.

| Example 6l |
| --- |
| HPLC-MS (Method): Z017_S04   MS: 236 (M*)$^+$ |
| R$_t$ [min]: 0.89 |

Example 6m

Example 6m is synthesised in analogy to example 6l. Starting materials: 2-chloro-pyrimidine-5-carbaldehyde (300 mg; 2.11 mmol) and 2-Fluoro-6-methylphenol (292 mg; 2.32 mmol).

Obtained: 500 mg used as such in the next step (content 75%).

| Example 6m | |
| --- | --- |
| HPLC-MS (Method): Z017_S04 | MS: 265 |
| R$_t$ [min]: 0.92 | (M + H + MeOH)$^+$ |

EXEMPLARY EMBODIMENTS

Example 20

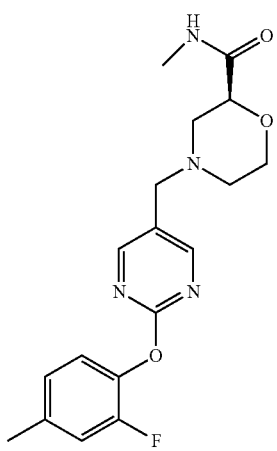 [SMILES: CNC(=O)[C@@H]1CN(Cc2cnc(Oc3ccc(C)cc3F)nc2)CCO1]

Example 6a (100 mg; 0.43 mmol) and Example 1a (68.3 mg, 0.47 mmol) were dissolved in THF (3 ml); DIPEA (0.11 ml; 0.60 mmol) was added and the reaction mixture was stirred 30 min. at room temperature; NaBH(OAc)$_3$ (137 mg, 0.65 mmol) was then added and the mixture was the stirred 18 hours at room temperature. The reaction mixture was then diluted with MeOH (3 ml) and the obtained solution was filtered with a syringe filter and purified via preparative HPLC. Obtained 49 mg of the desired compound.

| Example 20 | |
|---|---|
| HPLC-MS Method: Z003_S05; $R_t$ [min]: 1.02 | MS: 361(M + H)⁺ |
| Chiral SFC Method: I_SA_20_IPA_NH₃_001 | $R_t$ [min]: 2.82; e.e. 100% |
| ¹H NMR (400 MHz, DMSO-$d_6$) δ ppm: 1.94 (m, 1 H); 2.12 (m, 1 H); 2.34 (s, 3 H); 2.55-2.59 (m, 3H); 2.60-2.66 (m, 1 H); 2.89 (m, 1 H); 3.50-3.60 (m, 3 H); 3.83-3.90 (m, 2 H); 7.06 (m, 1 H); 7.19 (m, 1 H); 7.25 (m, 1 H); 7.64-7.72 (m, 1 H); 8.55 (s, 2 H). | |

Example 21

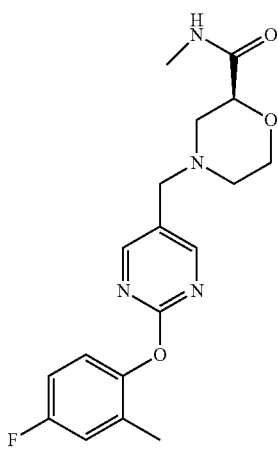 [SMILES: CNC(=O)[C@@H]1CN(Cc2cnc(Oc3ccc(F)cc3C)nc2)CCO1]

Example 21 was synthesised in analogy to example 20.

Starting materials: Example 6b (100 mg; 0.43 mmol)+Example 1a (67 mg, 0.47 mmol). The crude was purified via preparative HPLC. Obtained 120 mg of the desired compound.

| Example 21 | |
|---|---|
| HPLC-MS Method: Z003_S05; $R_t$ [min]: 1.01 | MS: 361 (M + H)⁺ |
| Chiral SFC Method: I_SA_20_IPA_NH₃_001 | $R_t$ [min]: 2.20 |
| ¹H NMR (400 MHz, DMSO-$d_6$) δ ppm: 1.94 (m, 1 H); 2.07 (s, 3 H); 2.12 (m, 1 H); 2.57 (m, 3 H); 2.60-2.66 (m, 1 H); 2.90 (m, 1 H); 3.50 (s, 2 H); 3.56 (m, 1 H); 3.83-3.90 (m, 2 H); 7.03-7.10 (m, 1 H); 7.15-7.20 (m, 2 H); 7.64-7.71 (m, 1 H); 8.54 (s, 2 H). | |

Example 22

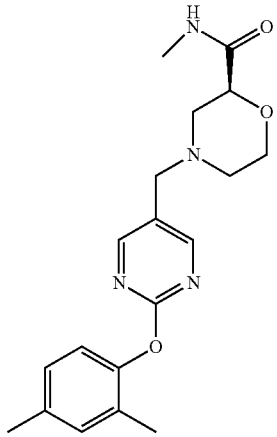 [SMILES: CNC(=O)[C@@H]1CN(Cc2cnc(Oc3ccc(C)cc3C)nc2)CCO1]

Example 22 was synthesised in analogy to example 20.

Starting materials: Example 6c (100 mg; content 90%; 0.39 mmol) and Example 1a (62.5 mg, 0.43 mmol). The crude was purified by preparative HPLC. Obtained 116 mg of the desired compound.

| Example 22 | |
|---|---|
| HPLC-MS Method: Z003_S05; $R_t$ [min]: 1.06 | MS: 357 (M + H)⁺ |
| Chiral SFC Method: I_SA_20_IPA_NH₃_001 | $R_t$ [min]: 3.01 e.e. 100% |
| ¹H NMR (400 MHz, DMSO-$d_6$) δ ppm: 1.94 (m, 1 H); 2.01 (s, 3 H); 2.12 (m, 1 H); 2.29 (s, 3 H); 2.55-2.59 (m, 3 H); 2.60-2.66 (m, 1 H); 2.90 (m, 1 H); 3.45-3.59 (m, 3 H); 3.83-3.90 (m, 2 H); 6.96-7.05 (m, 2 H); 7.10 (m, 1 H); 7.64-7.71 (m, 1 H); 8.51 (s, 2 H). | |

Example 23

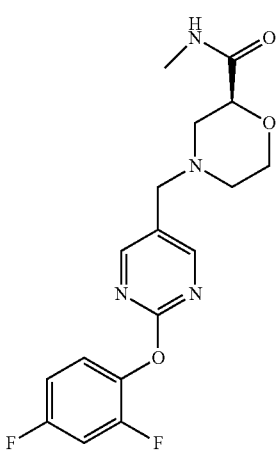 [SMILES: CNC(=O)[C@@H]1CN(Cc2cnc(Oc3ccc(F)cc3F)nc2)CCO1]

Example 23 was synthesised in analogy to example 20.

Starting materials: Example 6d (100 mg; 0.42 mmol) and Example 1a (67 mg, 0.47 mmol). The crude was purified by preparative HPLC.

| Example 23 | |
|---|---|
| HPLC-MS; Method: Z003_S05; | MS: 365 (M + H)⁺ |
| $R_t$ [min]: 0.99 | |
| Chiral SFC Method: | $R_t$ [min]: 2.07 e.e. 100% |
| I_SA_20_IPA_NH$_3$ _001 | |
| ¹H NMR (400 MHz, DMSO-d$_6$) δ ppm: 1.95 (m, 1 H); 2.09-2.16 (m, 1 H); 2.55-2.59 (m, 3 H); 2.60-2.66 (m, 1 H); 2.89 (m, 1 H); 3.48-3.59 (m, 3 H); 3.83-3.89 (m, 2 H); 7.13-7.19 (m, 1 H); 7.43-7.51 (m, 2 H); 7.66-7.71 (m, 1 H); 8.58 (s, 2 H). | |

Example 24

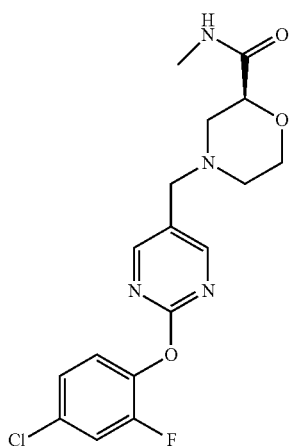 [SMILES: CNC(=O)[C@@H]1CN(Cc2cnc(Oc3ccc(Cl)cc3F)nc2)CCO1]

Example 24 was synthesised in analogy to example 20.

Starting materials: Example 6e (100 mg; content 75%; 0.30 mmol) and Example 1a (47 mg, 0.33 mmol). The crude was purified by preparative HPLC.

| Example 24 | |
|---|---|
| HPLC-MS; Method: Z003_S05; $R_t$ [min]: 1.07 | MS: 381 and 383 (M + H)⁺; Isotopic pattern for 1 Cl observed |
| Chiral SFC Method: I_SA_20_IPA_NH$_3$ _001 | $R_t$ [min]: 2.99; e.e. 100% |
| ¹H NMR (400 MHz, DMSO-d$_6$) δ ppm: 1.95 (m, 1 H); 2.13 (m, 1 H); 2.57 (m, 3 H); 2.61-2.67 (m, 1H); 2.89 (m, 1 H); 3.48-3.59 (m, 3 H); 3.83-3.90 (m, 2 H); 7.36 (m, 1 H); 7.48 (m, 1 H); 7.61-7.72 (m, 2 H); 8.58 (s, 2 H). | |

Example 25

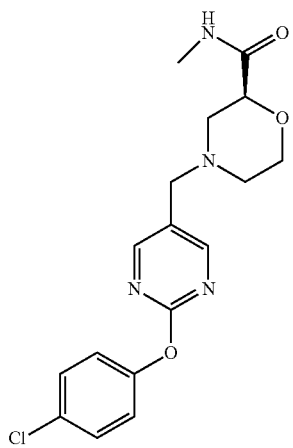 [SMILES: CNC(=O)[C@@H]1CN(Cc2cnc(Oc3ccc(Cl)cc3)nc2)CCO1]

Example 25 was synthesised in analogy to example 20.

Starting materials: Example 6f (100 mg; content 85%; 0.36 mmol) and Example 1a (57.5 mg, 0.04 mmol). The crude was purified by preparative. Obtained 77 mg.

| Example 25 | |
|---|---|
| HPLC-MS; Method: Z003_S05; $R_t$ [min]: 1.04 | MS: 363 and 365 (M + H)⁺; Isotopic pattern for 1 Cl observed |
| Chiral SFC Method: : I_SA_20_IPA_NH$_3$ _001 | $R_t$ [min]: 3.81; e.e. 100% |
| ¹H NMR (400 MHz, DMSO-d$_6$) δ ppm: 1.94 (m, 1 H); 2.07-2.16 (m, 1 H); 2.54-2.59 (m, 3 H); 2.61-2.67 (m, 1 H); 2.87-2.93 (m, 1 H); 3.47-3.59 (m, 3 H); 3.84-3.89 (m, 2 H); 7.27 (m, 2 H); 7.48 (m, 2 H); 7.65-7.70 (m, 1H); 8.56 (s, 2 H). | |

Example 26

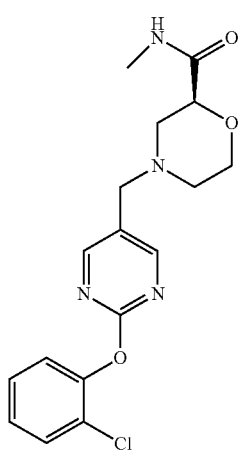 [SMILES: CNC(=O)[C@@H]1CN(Cc2cnc(Oc3ccccc3Cl)nc2)CCO1]

Example 26 was synthesised in analogy to example 20.

Starting materials: Example 6g (100 mg; content 70%; 0.30 mmol) and Example 1a (47 mg, 0.33 mmol). The crude was purified by preparative HPLC.

| Example 26 | |
|---|---|
| HPLC-MS; Method: Z003_S05; $R_t$ [min]: 0.99 | MS: 363 and 365 (M + H)$^+$; Isotopic pattern for 1 Cl observed |
| Chiral SFC Method: : I_SA_20_IPA_NH$_3$_001 | $R_t$ [min]: 3.38; e.e. 100% |
| $^1$H NMR (400 MHz, DMSO-d$_6$) δ ppm: 1.95 (m, 1 H); 2.07-2.16 (m, 1 H); 2.57 (m, 3 H); 2.64 (m, 1 H); 2.90 (m, 1 H); 3.47-3.60 (m, 3 H); 3.83-3.90 (m, 2 H); 7.29-7.35 (m, 1 H); 7.39-7.45 (m, 2 H); 7.59 (m, 1 H); 7.64-7.71 (m, 1 H); 8.56 (s, 2 H). | |

Example 27

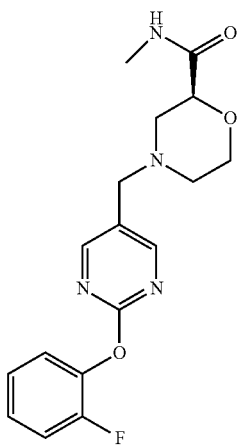 [SMILES: CNC(=O)[C@@H]1CN(Cc2cnc(Oc3ccccc3F)nc2)CCO1]

Example 27 was synthesised in analogy to example 20.

Starting materials: Example 6h (100 mg; 0.46 mmol) and Example 1a (72.7 mg, 0.50 mmol). The crude was purified by preparative HPLC. Obtained 70 mg.

| Example 27 | |
|---|---|
| HPLC-MS; Method: Z003_S05; $R_t$ [min]: 0.95 | MS: 347 (M + H)$^+$ |
| Chiral SFC Method: : I_SA_20_IPA_NH$_3$_001 | $R_t$ [min]: 2.50; e.e. 100% |
| $^1$H NMR (400 MHz, DMSO-d$_6$) δ ppm: 1.95 (m, 1 H); 2.12 (m, 1 H); 2.56-2.59 (m, 3 H); 2.61-2.67 (m, 1H); 2.89 (m, 1 H); 3.46-3.59 (m, 3 H); 3.82-3.91 (m, 2 H); 7.24-7.43 (m, 4 H); 7.63-7.74 (m, 1 H); 8.57 (s, 2 H). | |

Example 28

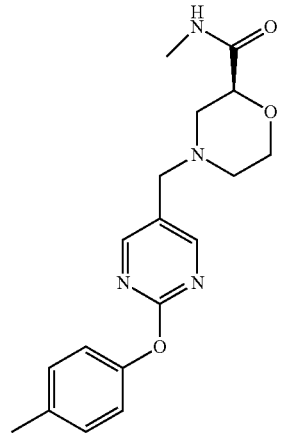 [SMILES: CNC(=O)[C@@H]1CN(Cc2cnc(Oc3ccc(C)cc3)nc2)CCO1]

Example 28 was synthesised in analogy to example 11.

Starting materials: Example 6i (277 mg; 50% content; 0.65 mmol) and Example 1a (116.5 mg; content 80%; 1.0 mmol). The crude was purified by preparative HPLC. Obtained 93 mg.

| Example 28 | |
|---|---|
| HPLC-MS; Method: Z011_S03; $R_t$ [min]: 0.866 | MS: 343 (M + H)$^+$ |
| Chiral SFC Method: : I_SA_20_IPA_NH$_3$_001 | $R_t$ [min]: 2.96; e.e. 99% |
| $^1$H NMR (400 MHz, DMSO-d$_6$) δ ppm: 1.87-2.01 (m, 1 H); 2.05-2.18 (m, 1 H); 2.32 (s, 3 H); 2.54-2.67 (m, 4 H); 2.90 (m, 1 H); 3.49 (m, 2 H); 3.56 (m, 1 H); 3.80-3.93 (m, 2 H); 7.07 (m, 2 H); 7.22 (m, 2 H); 7.68 (m, 1 H); 8.53 (s, 2 H). | |

Example 32

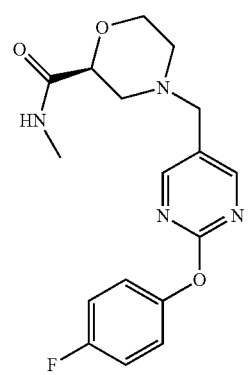 [SMILES: CNC(=O)[C@@H]1CN(Cc2cnc(Oc3ccc(F)cc3)nc2)CCO1]

Example 32 was synthesised in analogy to Example 20.

Starting materials: Example 6j (100 mg; 0.46 mmol) and Example 1a (72 mg; 0.50 mmol). The crude was purified by preparative.

| Example 32 | |
|---|---|
| HPLC-MS; Method: Z003_S05; | MS: 347 (M + H)⁺ |
| $R_t$ [min]: 0.95 | |
| Chiral SFC Method: : | $R_t$ [min]: 2.56; e.e. 100% |
| I_SA_20_IPA_NH₃ _001 | |
| ¹H NMR (400 MHz, DMSO-d₆) δ ppm: 1.94 (m, 1 H); 2.12 (m, 1 H); 2.56-2.59 (m, 3 H); 2.62-2.69 (m, 1 H); 2.90 (m, 1 H); 3.45-3.60 (m, 3 H); 3.82-3.91 (m, 2 H); 7.24-7.28 (m, 4 H); 7.68 (m, 1 H); 8.55 (s, 2 H). | |

Example 33

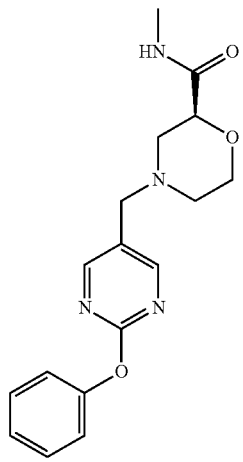 [SMILES: CNC(=O)[C@@H]1CN(Cc2cnc(Oc3ccccc3)nc2)CCO1]

Example 33 was synthesised in analogy to Example 20.

Starting materials: Example 6k (100 mg; 0.50 mmol) and Example 1a (79.2 mg; 0.55 mmol). The crude was purified via preparative HPLC. Obtained 120 mg of the desired compound.

| Example 33 | |
|---|---|
| HPLC-MS; Method: Z011_S03; | MS: 329 (M + H)⁺ |
| $R_t$ [min]: 0.80 | |
| Chiral SFC Method: : | $R_t$ [min]: 3.06; e.e. 100% |
| I_SA_20_IPA_NH₃ _001 | |
| ¹H NMR (400 MHz, DMSO-d₆); δ ppm: 1.95 (m, 1 H); 2.08-2.16 (m, 1 H); 2.58 (m, 3 H); 2.65 (m, 1 H); 2.91 (m, 1 H); 3.49-3.60 (m, 3 H); 3.79-3.94 (m, 2 H); 7.18-7.28 (m, 3 H); 7.43 (m, 2 H); 7.62-7.73 (m, 1 H); 8.55 (s, 2 H). | |

Example 34

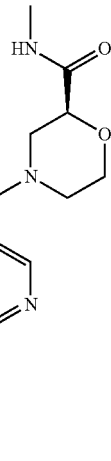

Example 34 was synthesised in analogy to Example 20.

Starting materials: Example 6l (120 mg; 0.51 mmol) and Example 1a (80.6 mg; 0.56 mmol). The crude was purified via preparative HPLC. Obtained 102 mg of the desired compound.

| Example 34 | |
|---|---|
| HPLC-MS; Method: Z003_S05; | MS: 365 (M + H)⁺ |
| $R_t$ [min]: 0.98 | |
| Chiral SFC Method: : | $R_t$ [min]: 2.28; e.e. 100% |
| I_SA_20_IPA_NH₃ _001 | |
| ¹H NMR (400 MHz, DMSO-d₆); δ ppm: 1.97 (m, 1 H); 2.13 (m, 1 H); 2.55-2.66 (m, 4 H); 2.90 (m, 1 H); 3.51-3.59 (m, 3 H); 3.82-3.92 (m, 2 H); 7.26-7.42 (m, 3 H); 7.63-7.74 (m, 1 H); 8.61 (s, 2 H). | |

Example 35

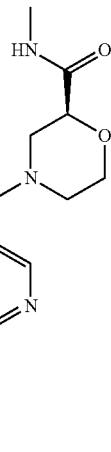

Example 35 was synthesised in analogy to Example 20.

Starting materials: Example 6m (140 mg; content 75%; 0.45 mmol) and Example 1a (71.7 mg; 0.50 mmol). The crude was purified via preparative HPLC. Obtained 115 mg of the desired compound.

| Example 35 | |
|---|---|
| HPLC-MS; Method: Z003_S05; R$_t$ [min]: 1.01 | MS: 361 (M + H)$^+$ |
| Chiral SFC Method: : I_SA_20_IPA_NH$_3$_001 | R$_t$ [min]: 2.3; e.e. 100% |
| $^1$H NMR (400 MHz, DMSO-d$_6$); δ ppm: 1.96 (m, 1 H); 2.08-2.17 (m, 4 H); 2.58 (m, 3 H); 2.60-2.66 (m, 1 H); 2.90 (m, 1 H); 3.49-3.60 (m, 3 H); 3.83-3.90 (m, 2 H); 7.14-7.22 (m, 3 H); 7.68 (m, 1 H); 8.56 (s, 2 H). | |

What is claimed is:

1. A compound of formula A

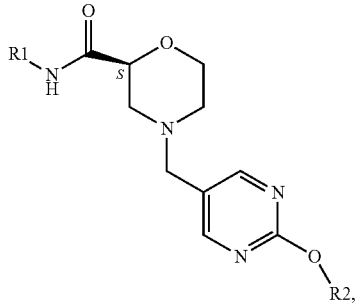

or a pharmaceutically acceptable salt thereof, wherein,

R$^1$ is selected from the group consisting of methyl, ethyl, propyl, iso-propyl, cyclopropyl, H$_3$C—CH$_2$—CH$_2$—CH$_2$—, and cyclobutyl; and R$^2$ is phenyl which is optionally substituted with 1, 2 or 3 substituents selected from the group consisting of fluoro, chloro, methyl, ethyl, and cyclopropyl.

2. The compound according to claim 1, or a pharmaceutically acceptable salt thereof, wherein R$^1$ is methyl; and
R$^2$ is selected from the group consisting of:

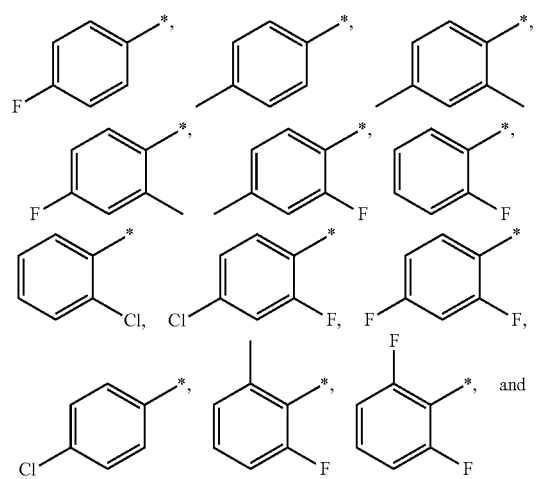

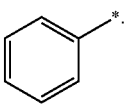

3. The (S)-enantiomer according to claim 1, or a pharmaceutically acceptable salt thereof, selected from the group consisting of:

| Ex. | |
|---|---|
| 20 | 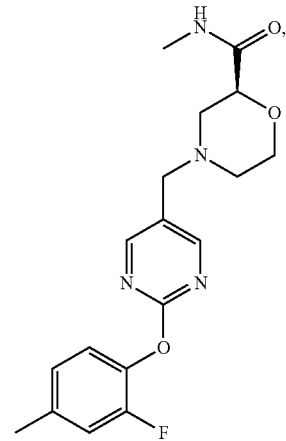 [SMILES: CNC(=O)[C@@H]1CN(Cc2cnc(Oc3ccc(C)cc3F)nc2)CCO1] |
| 21 | 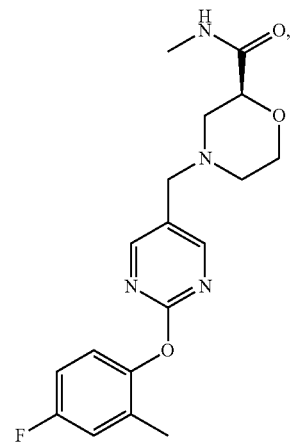 [SMILES: CNC(=O)[C@@H]1CN(Cc2cnc(Oc3ccc(F)cc3C)nc2)CCO1] |
| 22 | 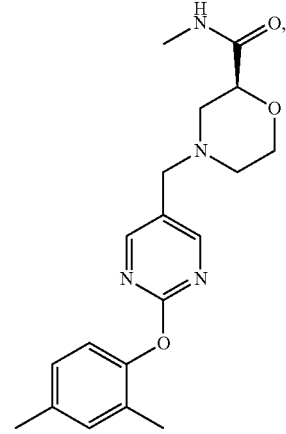 [SMILES: CNC(=O)[C@@H]1CN(Cc2cnc(Oc3ccc(C)cc3C)nc2)CCO1] |

| Ex. | |
|---|---|
| 23 | 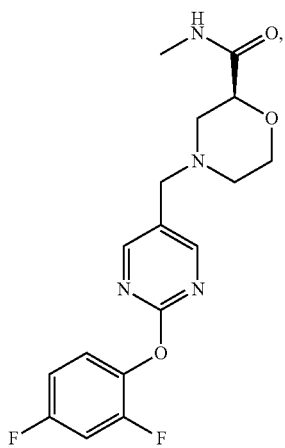 [SMILES: CNC(=O)[C@@H]1CN(Cc2cnc(Oc3ccc(F)cc3F)nc2)CCO1] |
| 24 | 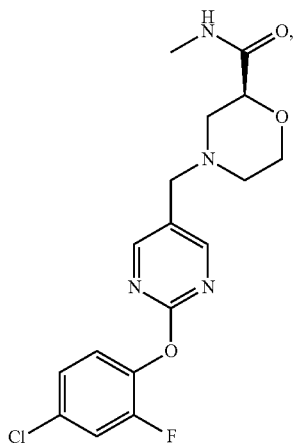 [SMILES: CNC(=O)[C@@H]1CN(Cc2cnc(Oc3ccc(Cl)cc3F)nc2)CCO1] |
| 25 | 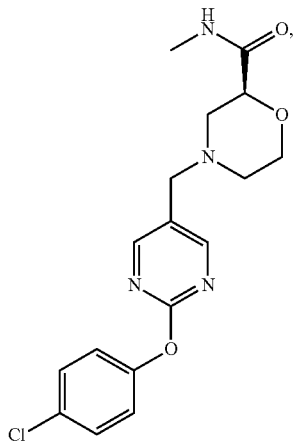 [SMILES: CNC(=O)[C@@H]1CN(Cc2cnc(Oc3ccc(Cl)cc3)nc2)CCO1] |
| 26 | 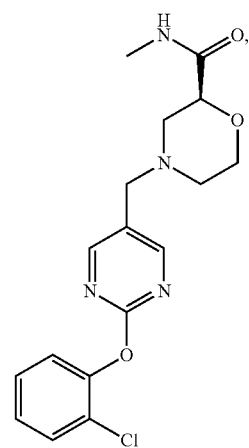 [SMILES: CNC(=O)[C@@H]1CN(Cc2cnc(Oc3ccccc3Cl)nc2)CCO1] |
| 27 | 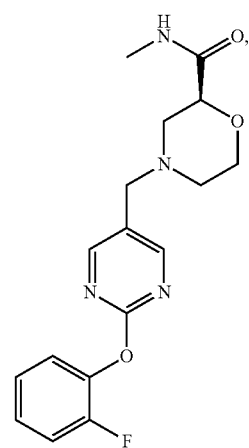 [SMILES: CNC(=O)[C@@H]1CN(Cc2cnc(Oc3ccccc3F)nc2)CCO1] |
| 28 | 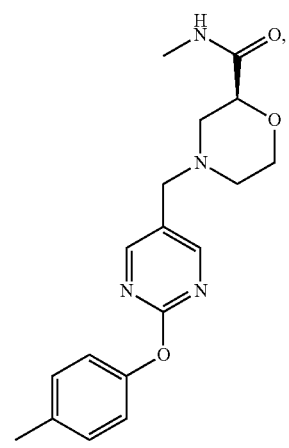 [SMILES: CNC(=O)[C@@H]1CN(Cc2cnc(Oc3ccc(C)cc3)nc2)CCO1] |

| Ex. | |
|---|---|
| 32 | 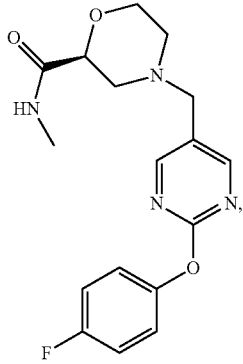 [SMILES: CNC(=O)[C@@H]1CN(Cc2cnc(Oc3ccc(F)cc3)nc2)CCO1] |
| 33 | 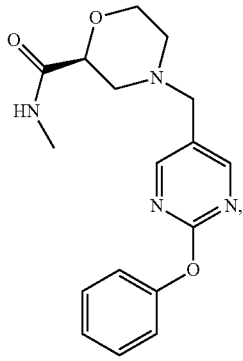 [SMILES: CNC(=O)[C@@H]1CN(Cc2cnc(Oc3ccccc3)nc2)CCO1] |
| 34 | 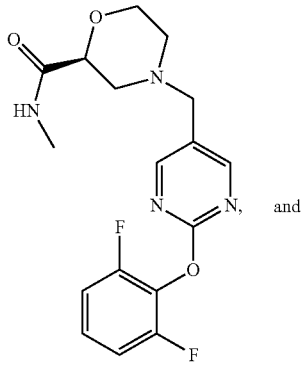 [SMILES: CNC(=O)[C@@H]1CN(Cc2cnc(Oc3c(F)cccc3F)nc2)CCO1 ; "and"] and |

| Ex. | |
|---|---|
| 35 | 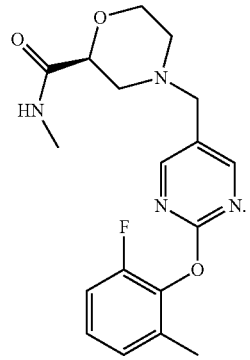 [SMILES: CNC(=O)[C@@H]1CN(Cc2cnc(Oc3c(C)cccc3F)nc2)CCO1] |

4. A pharmaceutically acceptable salt of a compound according to claim 1.

5. A method for treating bipolar disorders selected from a group consisting of: bipolar I disorder; bipolar 1 disorder with depressed, hypomanic, manic and mixed form features; bipolar II disorder; bipolar II disorder with a depressive episode; and major depressive episode with or without concomitant anxious distress, mixed features, melancholic features, atypical features, mood-congruent psychotic features, mood-incongruent psychotic features, or catatonia; the method comprising administering a pharmaceutically effective amount of a compound of formula A according to claim 1, or a pharmaceutically acceptable salt thereof, to a patient in need thereof.

6. A method for treating single depressive episode, recurrent major depressive disorder, minor depressive disorder, depressive disorder with postpartum onset, or depressive disorders with psychotic symptoms, the method comprising administering a pharmaceutically effective amount of a compound of formula A according to claim 1, or a pharmaceutically acceptable salt thereof, to a patient in need thereof.

7. The method according to claim 5, wherein the compound of formula A, or a pharmaceutically acceptable salt thereof, is administered with another antidepressant drug, selected from a group consisting of: duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, and nortriptyline.

8. The method according to claim 5, wherein the patient is further being treated with behavioural therapy.

9. The method according to claim 6, wherein the compound of formula A, or a pharmaceutically acceptable salt thereof, is administered with another antidepressant drug selected from a group consisting of: duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, and nortriptyline.

10. The method according to claim 6, wherein the patient is further being treated with behavioural therapy.

11. A pharmaceutical composition comprising the compound according to claim 1, or a pharmaceutically acceptable salt thereof, in admixture with a pharmaceutically acceptable adjuvant, diluent and/or carrier.

* * * * *